| (12) | United States Patent<br>Yang et al. | (10) Patent No.: US 10,544,371 B2<br>(45) Date of Patent: Jan. 28, 2020 |
|---|---|---|

(54) CHANNEL REACTORS

(71) Applicant: IntraMicron, Inc., Auburn, AL (US)

(72) Inventors: Hongyun Yang, Auburn, AL (US); Troy Barron, Auburn, AL (US); Bruce Tatarchuk, Auburn, AL (US); Paul Dimick, Waverly, AL (US)

(73) Assignee: IntraMicron, Inc., Auburn, AL (US)

( * ) Notice: Subject to any disclaimer, the term of this patent is extended or adjusted under 35 U.S.C. 154(b) by 0 days.

(21) Appl. No.: 15/977,642

(22) Filed: May 11, 2018

(65) Prior Publication Data

US 2019/0345395 A1 Nov. 14, 2019

(51) Int. Cl.
*C10G 2/00* (2006.01)
*C07C 1/04* (2006.01)
*B01J 8/00* (2006.01)
*B01J 8/04* (2006.01)
*B01J 19/00* (2006.01)
(Continued)

(52) U.S. Cl.
CPC .............. *C10G 2/343* (2013.01); *B01J 8/24* (2013.01); *B01J 23/94* (2013.01); *B01J 38/10* (2013.01); *C07C 1/04* (2013.01)

(58) Field of Classification Search
CPC ....... B01J 8/18; B01J 8/24; B01J 19/00; B01J 19/24; B01J 23/00; B01J 23/90; B01J 23/94; B01J 38/00; B01J 38/04; B01J 38/10; C07C 1/00–04; C10G 2/00; C10G 2/30; C10G 2/32; C10G 2/34; C10G 2/342; C10G 2/343
See application file for complete search history.

(56) References Cited

U.S. PATENT DOCUMENTS 4,101,287 A 7/1978 Sweed
4,430,304 A 2/1984 Spurrier
(Continued)

FOREIGN PATENT DOCUMENTS

FR 2707186 1/1995
GB 2120119 11/1983
(Continued)

OTHER PUBLICATIONS

International Search Report for corresponding PCT application PCT/US2019/031993 dated Aug. 2, 2019.
(Continued)

*Primary Examiner* — Natasha E Young
(74) *Attorney, Agent, or Firm* — PABST Patent Group LLP

(57) ABSTRACT

Described is an industrial scale chemical reactor or reactor containing a shell having an inner wall, and at least one channel inside the shell. The shell has a circular, square, or rectangular cross-sectional area. All of the internal dimensions of the channel are greater than 10 mm, and optionally less than 50 mm. The channel has a rectangular cross-sectional area, and contains a catalyst bed containing catalyst particles and/or pieces containing catalyst particles packed inside the channel. The reactor has improved shell volume utilization, catalyst loading capacities, heat exchange efficiency, process intensification, or combinations thereof, compared to currently existing reactors. Exothermic reactions, such as the Fischer-Tropsch synthesis can be performed inside the channels of the reactor. Also described are methods of making the reactor.

21 Claims, 5 Drawing Sheets

(51) Int. Cl.
    *B01J 19/24*     (2006.01)
    *B01J 23/94*     (2006.01)
    *B01J 38/10*     (2006.01)
    *B01J 8/24*     (2006.01)

(56) References Cited

U.S. PATENT DOCUMENTS

| | | |
|---|---|---|
| 4,585,798 A | 4/1986 | Beuther |
| 5,036,032 A | 7/1991 | Iglesia |
| 5,733,839 A | 3/1998 | Espinoza |
| 6,075,062 A | 6/2000 | Zennaro |
| 6,136,868 A | 10/2000 | Culross |
| 6,262,131 B1 | 7/2001 | Arcuri |
| 6,353,035 B2 | 3/2002 | Manzer |
| 6,368,997 B2 | 4/2002 | Herron |
| 6,451,864 B1 | 9/2002 | Wang |
| 6,476,085 B2 | 11/2002 | Manzer |
| 6,490,880 B1 | 12/2002 | Walsh |
| 6,537,945 B2 | 3/2003 | Singleton |
| 6,558,634 B1 | 5/2003 | Wang |
| 7,084,180 B2 | 8/2006 | Wang |
| 8,420,023 B2 | 4/2013 | Tatarchuk |
| 8,444,939 B2 | 5/2013 | Bowe |
| 9,359,271 B2 | 6/2016 | Leviness |
| 9,492,803 B2 * | 11/2016 | Kosters ............... B01J 8/062 |
| 1,035,056 A1 | 7/2019 | Rathke |
| 2002/0028853 A1 | 3/2002 | Manzer |
| 2002/0188031 A1 | 12/2002 | Kibby |
| 2003/0105171 A1 | 6/2003 | Subramanian |
| 2015/0071835 A1 | 3/2015 | Feinstein |
| 2015/0171835 A1 | 3/2015 | Feinstein |
| 2016/0362611 A1 * | 12/2016 | Harris ............... C10G 2/30 |
| 2017/0189874 A1 | 7/2017 | Filippi et al. |

FOREIGN PATENT DOCUMENTS

| | | |
|---|---|---|
| WO | 2010130399 | 11/2010 |
| WO | 2017060361 | 4/2017 |

OTHER PUBLICATIONS

Writen Opinion for corresponding PCT application PCT/US2019/031993 dated Aug. 2, 2019.

* cited by examiner

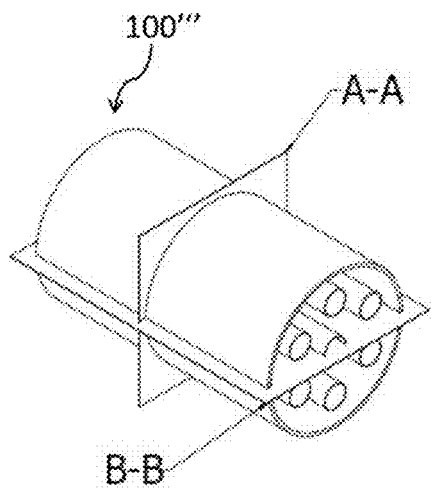
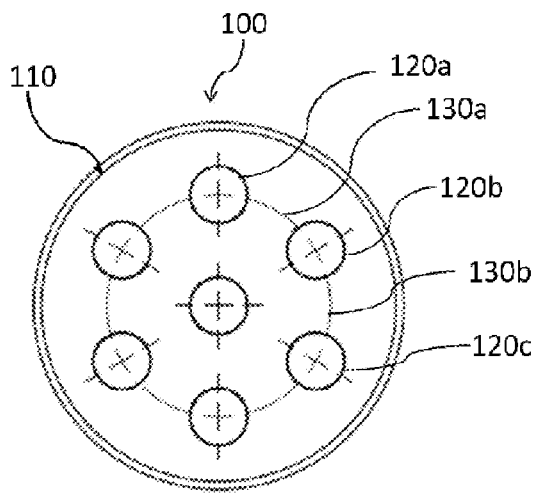
FIG. 1A
FIG. 1B
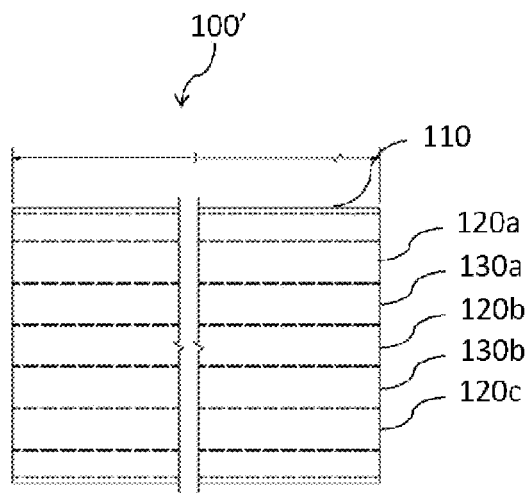
FIG. 1C
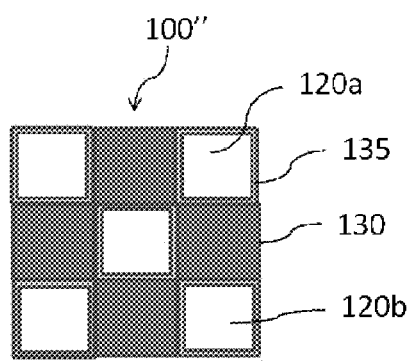
FIG. 2

CHANNEL REACTORS

FIELD OF THE INVENTION

The invention is generally in the field of channel reactors, particularly channel reactors for use in gas to liquid synthesis reactions, such as Fischer-Tropsch synthesis.

BACKGROUND OF THE INVENTION

Fischer-Tropsch synthesis (FTS) as well as many other gas-to-liquid (GTL) reactions are typically executed at high pressures (e.g. 10 atm-30 atm) and low temperatures (e.g. 200° C.-350° C.). Because of the high pressure and strong exothermic nature of FTS, fixed bed FTS reactors are typically shell-and-tube type, with many thin tubes located inside a large shell.

The FTS reactant, called synthesis gas or syngas, passes through thin tubes packed with catalyst particles, while a coolant, commonly pressurized hot water, passes through spaces between the thin tubes inside the shell. The pressurized hot water inside the shell removes heat generated from the FTS reaction to keep the reaction temperature constant or prevent wide temperature fluctuations. The circular cross-sectional area of the thin tubes along the length of FTS reactors distributes pressure isotropically along the walls of the reactor, to reduce or prevent deformation of the tube.

However, for a typical FTS shell-and-tube reactor, less than 50% of its volume is utilized for the FTS reaction.

Micro-channel reactors commonly use a cross-flow design, where the syngas and coolant flow perpendicularly to each other. However, their channel dimensions are up to 1 cm (10 mm), requiring the use of a large number of channels. See, e.g. U.S. Pat. No. 7,084,180 to Wang, et al., and U.S. Pat. No. 9,359,271 to LeViness, et al. Further, in LeViness, the catalyst in the channel reactors is in the form of a thin catalyst film wash-coated on the channel, which decreases the catalyst volume fraction to 2-4% of the shell volume. At this low catalyst loading level, process intensification is difficult to achieve.

U.S. Pat. No. 8,444,939 to Bowe and Lee-Tuffnell describes channel reactors with alternating reaction and cooling channels. However, these reactors are expensive and challenging to produce, as they require many channels and many channel connections. The catalyst is dispersed on a corrugated substrate. The corrugated structure further creates smaller, individual channels along the length of the reactor, which prevents radial diffusion of fluid flowing through the reactor. This results in low heterogeneous contact efficiencies, poor heat transfer, and the development of hotspots within the channel.

There is a need for improved channel reactors, particularly ones that permit reactions to be carried with improved process intensification.

Therefore, it is an object of the invention to provide channel reactors with improved process intensification.

It is another object of the invention to provide channel reactors with improved shell volume utilization, catalyst loading capacities, heat exchange efficiency, or combinations thereof.

It is a further object of the invention to provide improved methods and processes for conducting industrial scale chemical reactions, particularly exothermic reactions.

SUMMARY OF THE INVENTION

Industrial scale chemical reactors are described herein. The reactors contain a shell having an inner wall, and at least one channel inside the shell. All of the internal dimensions of the channel are greater than 10 mm, and optionally less than 50 mm. The channel has a rectangular cross-sectional area, in which a first internal dimension (height) is smaller than a second internal dimension (width). The channel contains a bed containing catalyst particles and/or pieces containing catalyst particles packed inside the channel.

The reactor has improved shell volume utilization, catalyst loading capacities, or heat exchange efficiency, or a combination thereof, compared to existing shell-and-tube reactors. These reactors are able to have a smaller shell volume, and fewer channels, i.e., part count, compared to typical shell-and-tube reactors, while achieving the same output or reaction rate for a given reaction.

The reactors can perform exothermic reactions, such as the FTS reaction. Accordingly, the reactors can be in a plant for making longer chain hydrocarbons from natural gas. Also described are methods of using the reactors.

BRIEF DESCRIPTION OF THE DRAWINGS

FIG. 1A is a perspective view of a portion of an exemplary shell-and-tube FTS reactor. FIG. 1B is a depiction of a cross-section of a portion of the reactor shown in FIG. 1A cut along a first plane, A-A. FIG. 1C is a depiction of another cross-section of the reactor depicted in FIG. 1A cut along a plane, B-B, which is perpendicular to the first plane, A-A.

FIG. 2 is an illustration of a channel reactor with alternating reaction and cooling channels. The walls of the reaction channels are wash-coated with a catalyst.

FIG. 3B shows two of the channels, without the shell. FIG. 3C further shows the cylindrical shell.

DETAILED DESCRIPTION OF THE INVENTION

I. Definitions

Figure 3A:
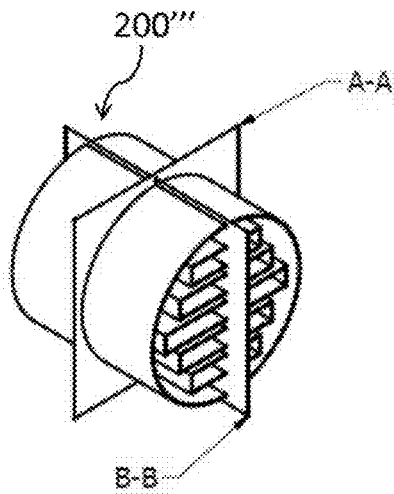
FIG. 3A is a perspective view of an exemplary industrial scale chemical reactor containing channels inside a cylindrical shell.

Internal dimension refers to a dimension, such as length, width, diameter, or height, that is measured inside the shell, e.g. the channel.

Macro-channel refers to a channel of a reactor for which all of its internal dimensions are greater than 10 mm.

Reactor volume can be calculated by multiplying the volume of a single reactor channel by the number of channels, or by multiplying the volume of a single reactor tube by the number of tubes. The volume of a reactor channel or tube is determined using the internal dimensions of the reactor's channel(s) or tube(s), in the case of a shell-and-tube reactor.

II. Industrial Scale Chemical Reactors

The reactors described herein generally have improved shell volume utilization, improved catalyst loading capacities, improved heat exchange efficiency, decreased cost, or decreased complexity, or a combination thereof, compared to currently available channel reactors.

The industrial scale chemical reactors contain a shell having an inner wall, and at least one channel inside the shell. The shell contains an inlet for a reactant fluid to flow into the channel(s), and an outlet for a product fluid to flow out of the channel(s) and exit the reactor. The shell can also contain a second inlet and a second outlet for a heat exchange fluid to flow into and out of the reactor, respectively. The heat exchange fluid flows around the channel(s), not in the channel(s).

The reactor can be used to perform exothermic or endothermic reactions. Preferably, the reaction is an exothermic reaction, such as the FTS reaction. The reactor has improved shell volume utilization, improved catalyst loading capacities, or improved heat exchange efficiency, or a combination thereof, compared to currently existing reactors. Further, these reactors typically have a smaller shell volume and fewer channels, i.e., part count, compared to typical shell-and-tube reactors, while achieving the same output at the same reaction rate at reduced costs. Preferably, the shell has a circular, square, or rectangular cross-sectional area. The flow of fluids (reactant fluid, product fluid, and/or heat exchange fluid) through the reactor can be laminar, turbulent, or both.

The channel has an inlet (for example 201 in FIG. 3D or FIG. 4C) for a reactant fluid and an outlet (for example 201' in FIG. 3D or FIG. 4C) for a product fluid. All of the internal dimensions of the channel are greater than 10 mm, and optionally less than 50 mm. The channel contains a catalyst bed (not shown in figures) containing catalyst particles and/or pieces (e.g. microfibrous medium) containing catalyst particles packed inside the channel (i.e., the space surrounded by the walls defining the channel). Optionally, the channel contains an internal packing structure located periodically along the axial direction of the channel. The channels optionally have an internal packing structure that enhances uniform flow distribution of fluid within the channels.

The reactor can include a gap between the channel and the inner wall of the shell, i.e., inner shell wall. In the case where the reactor has more than one channel, the reactor can also include a second gap between adjacent channels. The second gap can be smaller than the gap between the channel and the inner shell wall. In some forms, a heat exchange fluid, preferably, pressurized water flows through the gap and/or second gap. In some embodiments, the channels in the reactor do not contain a support structure inside of the channels. The reactors optionally contain additional support structures outside of the channels to prevent the channels from deforming. These support structures can also generate gaps (e.g. the second gaps) between adjacent channels through which the heat exchange fluid can flow.

1. Shell
A. Materials

The shell of any of the industrial scale chemical reactors can be made from any material that provides sufficient strength, dimensional stability and heat transfer characteristics for carrying out the desired reactions. Examples of suitable materials include metals (such as silver, zinc, copper, aluminum, nickel, iron, titanium, and chromium), metal alloys of any of the preceding metals, ceramics, glass, steel (e.g., stainless steel, carbon steel, etc), plastics (e.g., epoxy resins, UV cured resins, thermosetting resins, etc), monel, inconel, ceramics, glass, composites, quartz, silicon, and combinations thereof. Preferred materials include the any of the foregoing metals, their metal alloys, ceramics, glass, and combinations thereof.

B. Size

Generally, the design of the reactor is not limited by volumetric size, i.e., as determined by the dimensions of the channel(s). However, the reactor is generally larger than laboratory scale reactors. For example, laboratory scale reactors typically have reactor volumes in the range of a few millimeters (e.g. 2 mL) to a few liters (e.g. 1 L, 2 L, 3 L, or 5 L). In some forms, reactor volume is greater than $0.1$ $m^3$, optionally from $0.2$ $m^3$ to $1$ $m^3$, such as $0.37$ $m^3$. In some forms, the total volume of the shell, i.e., shell volume, ranges from less than a cubic meter to a few cubic meters, such as $2.0$ $m^3$, $1.0$ $m^3$, $0.5$ $m^3$, from $0.45$ $m^3$ to $0.60$ $m^3$, or $0.50$ $m^3$ to $0.60$ $m^3$.

2. Channels

Chemical reactions occurring within the reactor typically take place within the channels. The channels can have a flow through design, be periodically opened, or the flow can be variable in flow rate or direction. The number of channels within the reactor can be determined or limited by the height of the reactor, and the sizes of the gap and second gap. The width of the channel can be determined or limited by width of the reactor itself, or by the number of channels in the reactor.

The internal dimensions of each channel are greater than 10 mm, and optionally less than 50 mm. The height and width can be the same or different. The channel can have any length, depending on the purpose and conditions of the reaction being carried out. The length of the channel can be at least about two times the height or width, at least about five times the height or width, or at least about 10 times the height or width. Exemplary lengths of the channel are in the range of 1 m to 50 m, optionally in the range of 1 m to 10 m, or in the range of 5 m to 25 m, such as 1 m, 2 m, 3 m, 4 m, 5 m, 6 m, 10 m, 15 m, 20 m, 50 m, etc. The channel can have a cross-section having any non-cylindrical shape, for example, a square, rectangle, rhombus, hexagon, octagon, pentagon, etc. The shape and/or size of the cross-section of the macro-channel can vary over its length. For example, the height or width may taper from a relatively large dimension to a relatively small dimension, or vice versa, over the length of the macro-channel. Preferably, the cross-section of the macro-channel is uniform over its length.

A typical channel has a cross-sectional area having a first internal dimension and a second internal dimension. Preferably, the channel has a rectangular cross-sectional area, in which the first internal dimension is smaller than the second internal dimension. The first internal dimension can correspond with the height of the channel, and the second internal dimension can correspond with the width of the channel. The heights of each of the channels can be the same or different. Preferably, the heights of all of the channels are the same. The height can be greater than 10 mm and less than 150 mm, greater than 10 mm and less than 100 mm, inclusive, greater than 10 mm and less than 55 mm, greater than 10 mm and less than or equal to 50 mm. In some forms, the second internal dimension is the width of the channel. The widths of the channels can be the same or different. In some forms, the widths of all of the channels are the same. In some forms, the widths of all of the channels are different. In some forms, the width is between 3 and 400 times, inclusive, larger than the first internal dimension (e.g., height) of the channel, between 5 and 100 times, inclusive, larger than the height of the channel, or between 5 and 30 times, inclusive, larger than the height of the channel. In some forms, the channel is rectangular.

A. Materials

The channel walls are made of metals, metal alloys, or ceramics with thermal conductivity between 15 W/m·K and 2,200 W/m·K, inclusive, preferably between 15 W/m·K and 400 W/m·K, inclusive, for fast heat transfer from the channels to the heat exchange fluids. In the course of an exothermic reaction, the maximum temperature is generally achieved at the center of the rectangular channels.

Examples of metals that can be used to manufacture the channel walls include, but are not limited to, silver, zinc, copper, aluminum, nickel, iron, titanium, chromium, and metal alloys thereof. Optionally, the channel is formed from a metal such as silver, zinc, copper, aluminum, nickel, iron, titanium, chromium, or a metal alloy thereof.

B. Material Flowing Through Channels

The flow of fluid through the macro-channel can be along the length of the macro-channel normal to the height and width of the macro-channel. A chemical reaction can occur within the macro-channel, which converts a reactant fluid into a product fluid. The reactant fluid and/or product fluid can be in the form of a liquid and/or gas. Thus the fluid in the channel can be in the form of a liquid and/or gas.

In use, a reactant fluid enters the inlet and flows in the channel. Generally, the reactant fluid contains one or more reactants that chemically react in the presence of the catalyst bed. As the reactant fluid flows though the macro-channel, it is converted into the product. Thus, within the channel, the fluid is generally a combination of the reactants and products. However, for simplicity, the fluid inside the macro-channel is referred to herein as the fluid or the fluid in the channel. The fluid that exits the outlet is referred to as the product fluid.

A heat exchange fluid is generally in the form of a liquid and/or a gas and transmits heat energy to another substance, or absorbs heat from another substance. The substance is the channel, the fluid in the channel, or both. The heat exchange fluid can be a cooling fluid, i.e., one that absorbs heat from a channel and/or a fluid in a channel. Generally, the heat exchange fluid flows in gaps adjacent to the channel.

A reactant fluid contains a molecule that can undergo a chemical transformation into another molecule or product at the temperature and pressure conditions within a channel.

A product fluid contains a molecule or product arising from a chemical transformation of a molecule in a reactant fluid, at the temperature and pressure conditions within a channel.

In some forms, a reactant fluid, such as syngas, flows into an inlet of a channel, and a product fluid flows out of an outlet of the channel. The gas flow velocity or gas hourly space velocity (GHSV)) for the flow of the fluid through the channels can be between about 300 $hr^{-1}$ and about 20,000 $hr^{-1}$ (normal liters of feed/hour/liter of volume within the channels). Preferably, the fluid in the channel(s) has a GHSV between 400 $hr^{-1}$ and 10,000 $hr^{-1}$.

The temperature of the fluid within the channels can range between about 150° C. and about 400° C., inclusive, between about 150° C. and about 350° C., inclusive, between about 200° C. and about 350° C., inclusive, or between about 180° C. and about 330° C., inclusive. Preferably, the reactant fluid enters the inlet to the channel at a temperature between about 180° C. and about 330° C. Preferably, a reaction occurs in the channel at a temperature between 200° C. and about 350° C.

In some forms, the reactant fluid has a GHSV between 400 $hr^{-1}$ and 10,000 $hr^{-1}$, inclusive, at a temperature of 200-250° C. In some forms, these flow velocity and temperature ranges are for a Fischer-Tropsch catalyst. In some forms, the Fischer-Tropsch catalyst is cobalt-based.

In some forms, the reactant fluid, which is provided to an inlet of an industrial scale chemical reactor described herein, contains hydrogen gas and carbon monoxide, and optionally contains at least one aliphatic hydrocarbon having at least about five carbon atoms.

3. Catalyst Bed

One or more of the channels contain a bed containing one or more catalysts. The catalysts can be in the form of particles (e.g. extrudates, pellets, rings, powder, grains, or combinations thereof), microfibrous entrapped catalysts (MFEC), or a combination thereof. U.S. Pat. No. 8,420,023 to Tatarchuk, et al., describes MFEC, the contents of which are incorporated herein by reference. The bed can be in the form of a packed bed catalyst (i.e. a packed bed that contains catalyst, such as where the catalyst is in the form of extrudates, pellets, rings, powder, grains, or a combination thereof) or microfibrous entrapped catalyst (MFEC), or a combination thereof. Optionally the bed contains catalyst rings, metal foam, or ceramic foam, or a combination thereof. Optionally, the bed includes inert porous structures, such as ceramic foam, microfibrous media, gaps, ceramic rings, or a combination thereof.

The structure of the catalyst bed of the reactors described herein affords the design of channel reactors with significant advantages, such as heat flow and/or loading efficiencies, over currently available channel reactors. For example, the corrugated catalyst bed described in U.S. Pat. No. 8,444,939 to Bowe and Lee-Tuffnell, limits the height of the reactor to no more than 12 mm. Heights beyond this limit give rise to the formation of hot spots in the channels due to poor heat transfer. Further, the corrugated catalyst bed also creates smaller, individual channels along the length of the reactor, which prevent radial diffusion of fluid in the channels leading to heterogeneous contact inefficiencies.

The bed used in the channel reactors described herein allows for channels with heights two, three, or even four times larger than those disclosed in U.S. Pat. No. 8,444,939 to Bowe and Lee-Tuffnell. Further, the bed containing the catalyst, as described herein, prevents the development of hotspots within the channel.

In some forms, the catalyst can be any Fischer-Tropsch catalyst. The catalyst contains at least one catalytically active metal or oxide thereof. In some forms, the catalyst can include a catalyst support. In some forms, the catalyst can include at least one promoter. The catalyst can be a catalytically active metal, such as Co, Fe, Ru, Re, or Os, or a combination thereof. The support material can include alumina, zirconia, silica, aluminum fluoride, fluorided alumina, bentonite, ceria, zinc oxide, silica-alumina, silicon carbide, or a molecular sieve, or a combination thereof. The support material can include a refractory oxide. The promoter can include a Group IA, IIA, IIIB or IVB metal or oxide thereof, a lanthanide metal or metal oxide, or an actinide metal or metal oxide. In some forms, the promoter is Li, B, Na, K, Rb, Cs, Mg, Ca, Sr, Ba, Sc, Y, La, Ac, Ti, Zr, La, Ac, Ce, or Th, or an oxide thereof, or a mixture thereof. Examples of catalysts that may be used include those disclosed in U.S. Pat. Nos. 4,585,798; 5,036,032; 5,733,839; 6,075,062; 6,136,868; 6,262,131B1; 6,353,035B2; 6,368,997B2; 6,476,085B2; 6,451,864B1; 6,490,880B1; 6,537,945B2; 6,558,634B1; and U.S. Patent Publications 2002/0028853 A1; 2002/0188031A1; and 2003/0105171A1; these patents and patent publications being incorporated herein by reference for their disclosures of Fischer-Tropsch catalysts and methods for preparing such catalysts.

4. Gaps for Heat-Exchange Fluid Flow

The reactor can include a gap between the channel and the inner wall of the shell. In the case where the reactor has more than one channel, the reactor can also include a second gap between adjacent channels. The gap and/or second gap can independently run parallel, perpendicular, or both, to the channel. In some forms, the second gap is smaller than the gap between the channel and the inner wall of the shell. Preferably, the heights of the one or more gaps are not less than 5 mm, or not less than 10 mm. In some forms, the heights of the one or more second gaps are between 5 mm and 100 mm, inclusive. Suitable heights for the one or more gaps are in the range of 5 mm to 50 mm, optionally in the range of 5 mm to 20 mm, or in the range of 5 mm to 10 mm, such as 5 mm, 6 mm, 7 mm, 8 mm, 9 mm, 10 mm, 15 mm, 20 mm, 25 mm, and 50 mm.

5. Heat-Exchange Fluid

In general, a heat exchange fluid flows through the gap and/or second gap, and transmits or absorbs heat energy from or to a fluid (such as a fluid containing one or more reactants, and/or products) flowing through the channel. The heat exchange fluid can be a fluid such as pressurized water, steam, liquid water, air, gaseous nitrogen, other gases (e.g. inert gases, carbon monoxide), molten salt, oils such as mineral oil, and heat exchange fluids such as DOWTHERM® A and THERMINOL®, which are available from Dow-Union Carbide. Preferably, the heat exchange fluid is pressurized water, supplied under a pressure such that its boiling point is close to that of the required reaction temperature. For example, for a cobalt-based FTS reaction, the boiling point of pressurized water is around 220° C.

In general, the boiling point of the heat exchange fluid can be within about 5° C., 10° C., 20° C., or 30° C. of the reaction (e.g. FTS) temperature. Further, in some forms, the heat exchange fluid is supplied at a pressure ($P_o$) equal to that within the channel (Pt).

In general, the temperature difference between the heat exchange fluid at the outlet (for example 201' in FIG. 3D or FIG. 4C) or inlet (for example 201 in FIG. 3D or FIG. 4C) of the reactor and the temperature of the reaction is between 10° C. and 30° C., inclusive. The temperature of the heat exchange fluid at the inlet of the reactor can be between about 160° C. and about 400° C., inclusive, or between 200° C. and about 350° C., inclusive. Preferably, the temperature difference between the temperature of the heat exchange fluid at the outlet or inlet of the reactor and the temperature of the reaction is between 10° C. and 30° C., inclusive. Preferably, the temperature of the heat exchange fluid at the inlet is between 200° C. and 350° C.

In some forms, the heat exchange fluid and the fluid flowing in one or more channels flow in a co-current pattern, a counter-current pattern, or a cross-current pattern, or a combination thereof. In some forms, the heat exchange fluid and the fluid flowing in one or more channels flow in a co-current pattern. In some forms, the heat exchange fluid and the fluid flowing in one or more channels flow in a counter-current pattern.

In some forms, the heat exchange fluid undergoes a partial or full phase change as it flows through a gap. In the case of an exothermic reaction occurring inside the channel, this phase change can provide additional heat removal from the channels beyond that provided by convective cooling. An example of such a phase change would be an oil or water that undergoes boiling.

Generally, the heat exchange fluid is supplied at a flow rate such that the cooling fluid (in the case of an exothermic reaction) can remove the heat from fluid in the channel and keep the cooling fluid's temperature rise under a certain threshold temperature, such that the difference between the cooling fluid's outlet and inlet temperatures is within 10-30° C. In case saturation water is used, its flow rate can be much smaller due to its high heat capacity and high heat transfer coefficient. In case heat exchange fluids are used without phase changes, the cooling fluids are typically fed at high flow rates such that they can meet the temperature criteria described herein and also generate high heat transfer coefficients due to the resulting turbulence at high fluid velocities.

6. Support Structures in Gaps

Because of the large widths of these channels, deformation, such as swelling, under the typical pressure conditions in some reactions, such as the FTS reaction, can occur if the channels are used alone. Therefore, in some forms, the reactors described herein contain additional support structures (e.g. metal, welded metal bars, brackets, rods, etc,) outside of the channels to prevent the channels from deforming. At the same time, these support structures can also generate gaps (e.g. the second gaps) between adjacent channels through which the heat exchange fluid can flow. Another approach to prevent deformation of the channels includes adjusting the pressure outside ($P_o$) of the channels to balance it with the internal channel pressure ($P_i$) applied internally on the channel walls. Therefore, in some forms, a heat exchange fluid is supplied at a pressure ($P_o$) equal to that within the channel ($P_i$). In these instances, the heat exchange fluid is generally supplied at a pressure such that its boiling point is at a temperature that is within 5° C. to 30° C., lower than that of the reaction (e.g. FTS reaction) temperature, preferably the heat exchange fluid is provided at a pressure such that its boiling point is within 5° C. to 10° C. lower than that of the reaction temperature. For example, the boiling point of the heat exchange fluid can be within about 5° C., 10° C., 20° C., or 30° C. of the reaction (e.g. FTS) temperature. Typically, the pressure of the heat exchange fluid is within 20 atm, preferably within 10 atm or 5 atm of the pressure inside ($P_i$) the channel(s).

7. Internal Packing Structures in Channels

The channels can also have an internal packing structure that enhances uniform flow distribution of fluid within the channels. Undesired flow distribution can adversely affect the performance of the catalytic reactor, generate local hot spots inside the larger reactors, or both. These issues become more severe when long reactors are used. Accordingly, in some forms, inert porous structures such as ceramic foam, microfibrous media, gaps, ceramic rings, and combination thereof, that have high porosity (higher than the those of the catalyst bed) and larger opening sizes (larger than the packed catalyst particles or the fiber diameters in the case of microfibrous entrapped catalysts) can be included in the bed along the axial direction. In some forms the porous structures are located periodically in the axial direction. The fluid in a channel that contains such porous structures, passes through the porous structures and is re-distributed.

8. Shell Volume Utilization

The channels described herein occupy a higher proportion of the total volume of the reactor, i.e., increased shell volume utilization, compared to tubular channels. The channels also have increased catalyst loading capacities compared to non-tubular channels with catalysts wash-coated inside channel walls.

Shell volume utilization refers to the proportion of the volume of the shell occupied by the total volume of the channel(s) (i.e., the sum of the volume for each channel). The total volume of the channel(s) can be such that the channels occupy more than more than 50% of the shell volume, preferably more than 60% of the shell volume, more preferably more than 80% of the shell volume.

Shell volume utilization can be determined by dividing the total volume of the channel(s) by the shell volume. The shell volume utilization can increase to up to 50%, up to 60%, up to 70% or up to 80% for a reactor containing rectangular channels as described herein compared to a reactor having the same shell volume that contains round tubes.

A review of exemplary channels in prior reactors follows.

Referring to FIGS. 1B and 1C, fixed bed FTS reactors are typically shell-and-tube type 100 and 100', containing a large shell 110 with many thin tubes (or channels) 120a, 120b, 120c, etc., located inside the large shell 110. The thin tubes are separated by gaps 130a, 130b, etc.

The FTS reactant (synthetic gas or syngas) passes through tubes packed with catalyst particles, and a coolant, commonly pressurized hot water, passes through the shell. The pressurized hot water inside the shell removes the heat generated from the FTS reaction and keeps the reaction temperature constant.

The diameter of the round FTS tubes is determined by the maximum temperature rise within the tubes. For the given heat generation rate (S, [W/m$^3$]), effective thermal conductivity of the catalyst bed ($K_e$, [W/m·K]) and tube wall temperature (Tw, [K]), the maximum temperature (Tm, [K]) inside the FTS reactor tube is a function of tube diameter (d, [m]).

$$T_m = T_w + \frac{S}{16 K_e} d^2 \qquad \text{(Eq. 1)}$$

In order to achieve high selectivity to the desired FTS products, the difference between Tm and Tw (i.e., ΔT=Tm-Tw) must be kept low by using tubes with a small diameter (d) and catalyst beds with a high effective thermal conductivity (high $K_e$) and low heat generation rate (lower S) at both the laboratory and industrial scales. Effective thermal conductivity refers to the thermal conductivity of a heterogeneous system, i.e., the thermal conductivity of a substance influenced by another substance, as opposed to the actual conductivity that relates to a substance's bulk material. For a given maximum allowed ΔT (ΔT$_{max}$), the largest allowed tube diameter (d$_{max}$) can be defined as:

$$d_{max} = 4\sqrt{\frac{\Delta T_{max} K_e}{S}}. \qquad \text{(Eq. 2)}$$

For example, the maximum tube diameter can be limited to 10 cm (4 inches) for an FTS reactor filled with microfibrous entrapped catalyst with high thermal conductivity and high reactivity in order to keep the maximum temperature gradient within the FTS reactor less than 30° C. However, process intensification generally pushes the d$_{max}$ to the lower end. Because the heat generation rate (S) is proportional to the reaction rate and production rate of the FTS reaction, heat generation should be as high as possible for process intensification purposes. Therefore, in industry, very high gas velocities are employed to achieve high effective thermal conductivities, and small tubes with diameters between 0.5 inch and 1 inch are commonly used to minimize the difference between the tube wall (Tw) and maximum temperatures (Tm). The features of an exemplary pilot scale FTS shell-and-tube reactor are listed in Table 1, to provide a basis for comparison with other reactors.

TABLE 1

Features of an exemplary pilot FTS reactor (as a basis for comparison)

| Shell diameter (D) | 0.50 m | Tube gap (γ) | 7 mm |
|---|---|---|---|
| Tube array pattern | Square | Tube wall thickness | 2.5 mm |
| Tube diameter (d) | 25 mm | Tube length (L) | 6.0 m |
| Tube center distance | 32 mm | Tube count (Nt) | 124 |

FIGS. 1A, 1B, and 1C show general features of exemplary shell-and-tube reactors, in this case, containing seven tubes. Using the dimensions listed in Table 1 for an exemplary shell-and-tube reactor, the cross-sectional area of the shell is 0.19 m$^2$ and the total cross-sectional area of the tubes is 0.06 m$^2$, which is about 31% of that of the shell. Thus, a majority of the volume (69%) of this FTS reactor is not utilized for the FTS reaction.

Referring to FIG. 2, this reactor 100" has reaction channels 120a, 120b, etc, separated by a cooling channel 130. The reaction channels are wash-coated with a catalyst film 135. While the shell volume utilization in this reactor (having the same dimensions as listed in Table 1) can increase to approximately 50% compared to reactors depicted in FIGS. 1B and 1C, the wash-coated channels of FIG. 2 decrease the catalyst volume fraction to 2-4% of the shell volume (i.e., shell volume), making it difficult to achieve process intensification.

Figure 3B:
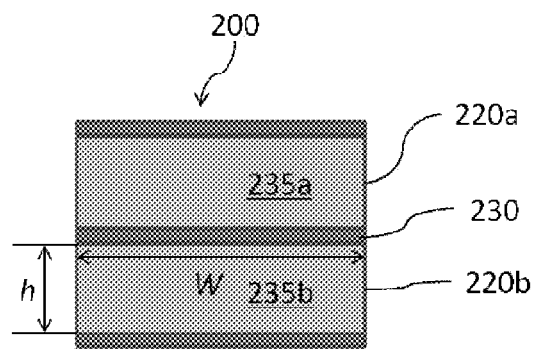
FIGS. 3B and 3C are illustrations of cross-sections of the reactor shown in FIG. 3A cut along a first plane, A-A, depicting channels separated by gaps (e.g. cooling gaps).

Referring to FIG. 3B, a reactor 200 can have more than one channel 220a, 220b, etc. These channels have much larger dimensions compared to channels in micro-channel reactors, optionally containing a catalyst bed that contains a catalyst 235a, 235b, etc. The channel(s) can be in a shell having a variety of different shapes, such as a cylindrical, rectangular, or square shell. The channels 220a and 220b are separated by a gap 230. The reactor 200 has a cross-sectional area having a first internal dimension, h, and a second internal dimension, W. W can be greater than h. In some forms, h and W can be the same. The heights of the channels can be the same or different. Preferably, the heights of the channels are the same. The widths of the channels can be the same or different. Preferably, the widths of the channels are the same. The reactor depicted in FIG. 3B has a higher shell volume utilization and higher catalyst loading, compared to that of the exemplified shell-and-tube reactor.

When W is much larger than h, most heat transfer occurs via the two big horizontal surfaces along the width. According to equation for classic heat transfer through a slab, the maximum allowed channel height (h$_{max}$) for heat transfer can be described as:

$$h_{max} = 2\sqrt{2}\sqrt{\frac{\Delta T_{max} K_e}{S}} \qquad \text{(Eq. 3)}$$

Referring to Table 2, for a macro-channel reactor filled with a bed containing a catalyst (Case 2, in Table 2) having the same catalyst packing (i.e., the same S and Ke and the same $\Delta T_{max}$), the maximum allowed channel height is smaller than the maximum allowed tube diameter, defined by:

$$h_{max} = \frac{d_{max}}{\sqrt{2}} \quad \text{(Eq. 4)}$$

where $d_{max}$ is the maximum allowed tube diameter. For a macro-channel reactor, the height of the channel is optionally 71% (i.e., $1/\sqrt{2}$) of the maximum allowed tube diameter for a tubular reactor filled with the same catalyst in same manner (e.g. packed bed or MFEC). Optionally, for a macro-channel reactor, the height of the channel is in the range of 60% to 80%, optionally 65% to 75% or 70% to 75%, of the maximum allowed tube diameter for a tubular reactor filled with the same catalyst in same manner (e.g. packed bed or MFEC).

If a thermally conductive catalyst structure, e.g. copper microfibrous entrapped catalyst (MFEC), is used, while $\Delta T_{max}$ and S remain constant, then $h_{max}$ can become larger (Case 3, Table 2). For example, because copper MFEC can have a thermal conductivity 16 times larger than that obtained in a packed bed (Case 2, Table 2), the height of the macro-channel reactor can be four times larger than that determined in Case 2.

Figure 3C:
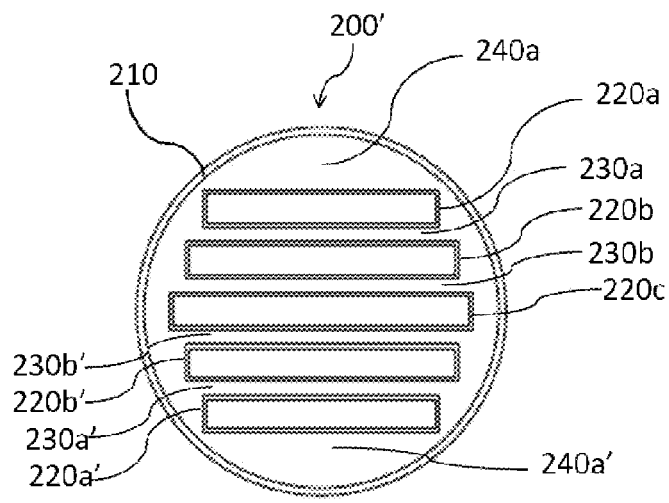
Figure 3D:
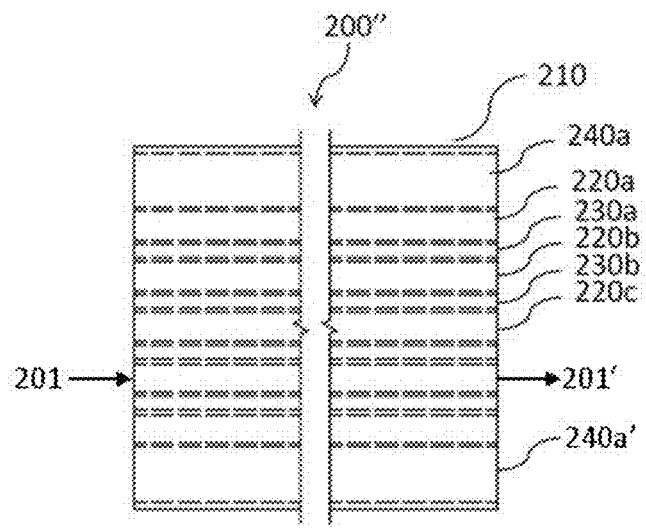
FIG. 3D is an illustration of another cross-section of the reactor of FIG. 3A cut along a second plane, B-B, which is perpendicular plane to the first plane, A-A.

Referring to FIGS. 3C and 3D, in some forms, the reactor 200' has a cylindrical shell 210 having a circular cross-sectional area. One or more channels 220a, 220b, 220c, 220a', are 220b' are located inside the cylindrical shell 210. The channels can have different widths (W). Typically, the channels have the same heights (h). By way of example, the dimensions (W×h) of the channels can be 10.5"×1.75" (220c), 8"×1.75" (220b, 220b'), and 6"×1.75" (220a, 220a'). The diameter of the cylindrical shell 210 can be 12.5". One or more gaps 240a, 240a', etc, are located between the one or more channels and the internal surface of the cylindrical shell 210. One or more second gaps 230a, 230a', 230b, and 230b' separate the channels from each other when there are two or more channels in the reactor. Preferably, the heights of the one or more gaps located between the one or more channels and the internal surface of the cylindrical shell are 5 mm or greater, or 10 mm or greater; however, generally the gaps are up to 100 mm in height. In some forms, the heights of the one or more second gaps are between 5 mm and 100 mm, inclusive. Suitable heights for the one or more second gaps, which separate the channels from each other, include 5 mm, 6 mm, 7 mm, 8 mm, 9 mm, 10 mm, 15 mm, 20 mm, 25 mm, and 50 mm.

The heat exchange fluid and the fluid flowing in one or more channels flow may flow in a co-current pattern, a counter-current pattern, or a cross-current pattern, or in a combination of these flow patterns thereof.

The channels 220a, 220b, 220c, 220a', are 220b' can each contain a catalyst bed that contains a catalyst.

Figure 4A:
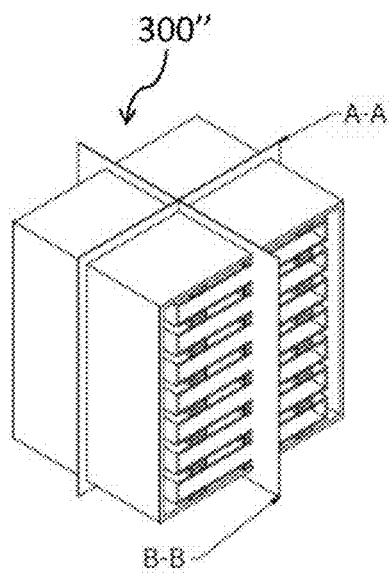
FIG. 4A is a perspective view of an exemplary industrial scale chemical reactor containing channels inside a square shell.
Figure 4B:
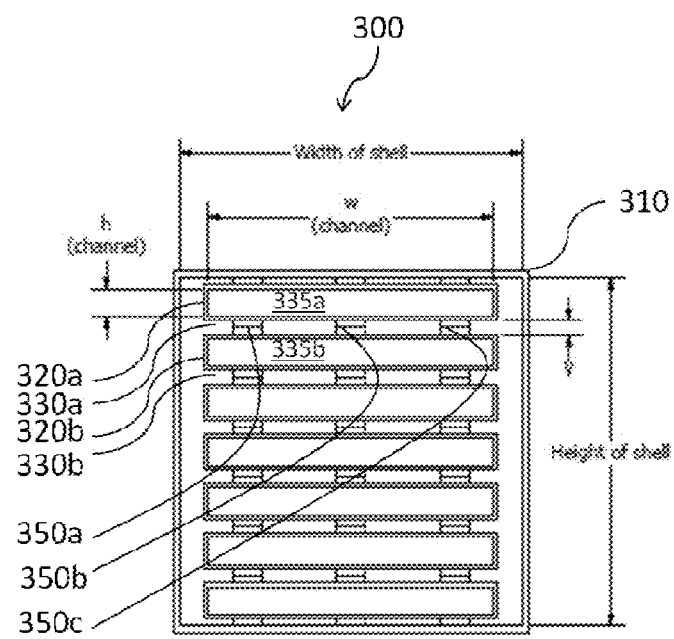
FIG. 4B is an illustration of the cross-section of the reactor shown in FIG. 4A cut along a first plane, A-A, showing macro-channels separated by gaps (e.g. cooling gaps).
Figure 4C:
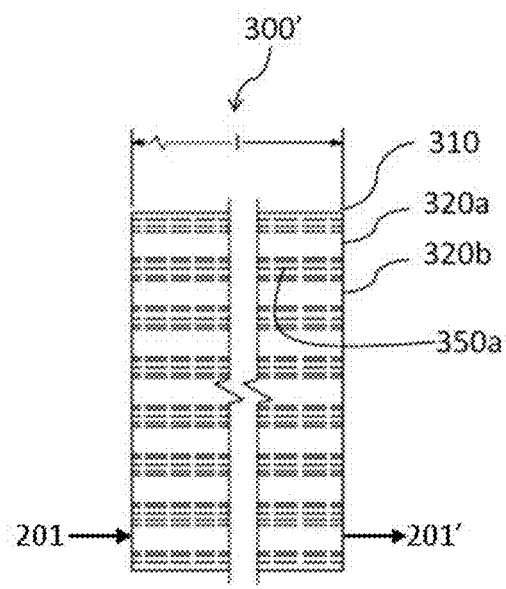
FIG. 4C is an illustration of a partial view of a cross-section of the reactor of FIG. 4A cut along a second plane, B-B, which is perpendicular to the first plane, A-A.

In some forms, the channels have uniform sizes, such as the same width and height. In these instances, a square shell can be used to further improve the packing efficiency of the channels within a reactor, i.e., the reactor has improved shell volume utilization. Referring to FIGS. 4B and 4C, the reactor 300 has a shell 310 having a square cross-sectional area. One or more rectangular channels 320a, 320b, etc, are located inside the shell 310. Optionally, the one or more rectangular channels 320a, 320b, etc, contain a catalyst bed that contains a catalyst 335a, 335b, etc. FIGS. 4B and 4C illustrate one form of the macro-channel concept. Optionally, the channel count can be higher than seven (as shown in FIGS. 4B and 4C). The dimensions of each channel are typically the same. For example, a macro-channel reactor filled with the same packed bed catalyst can have a width of 290 mm and a channel height of 17.7 mm ($25/\sqrt{2}$) (11.4"×0.7"), while the dimensions of the cross-sectional area of the shell can be 10"×10". The reactor 300 further contains support structures 350a, 350b, 350c, etc, between adjacent channels to prevent the channels from deforming. The support structures also support the second gaps (330a, 330b, etc,) between adjacent channels through which a heat exchange fluid can flow. The heights of the one or more second gaps located between adjacent channels can be between 5 mm and 100 mm, inclusive. Suitable heights for the one or more second gaps include 5 mm, 6 mm, 7 mm, 8 mm, 9 mm, 10 mm, 15 mm, 20 mm, 25 mm, and 50 mm. The heights of the one or more gaps located between a wall of the shell and a channel can be between 5 mm and 100 mm, inclusive. Suitable heights for the one or more gaps, which are located between a wall of the shell and a channel include 5 mm, 6 mm, 7 mm, 8 mm, 9 mm, 10 mm, 15 mm, 20 mm, 25 mm, and 50 mm.

Figure 5A:
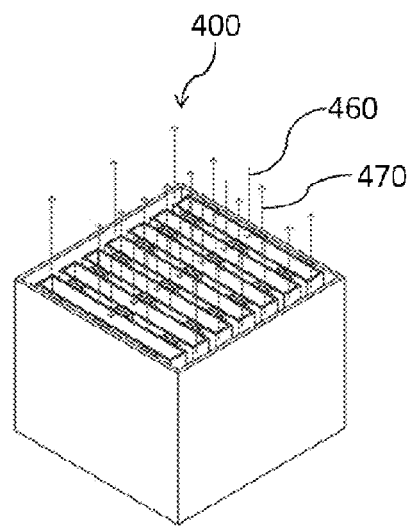
FIGS. 5A and 5B are illustrations of perspective views of an industrial scale chemical reactor showing relationships between fluid flow in the macro-channels and gaps between adjacent channels: counter-current (FIG. 5A) and co-current (FIG. 5B).
Figure 5B:
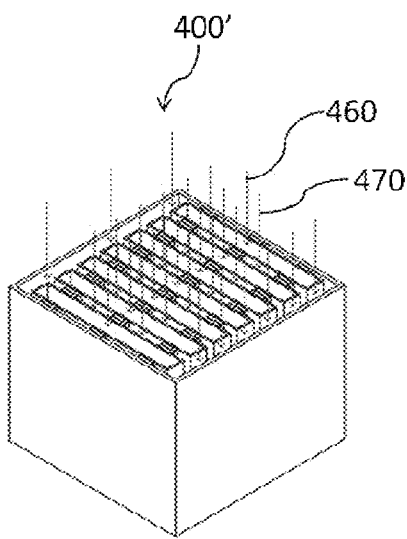

FIGS. 5A and 5B are perspective views of a reactor, such as that shown in FIG. 4B, depicting the relationships between fluids flowing in the channels and in the second gaps. In reactor 400 shown in FIG. 5A, the relationship between the directions 460 and 470 of fluid flow in the channels and second gaps, respectively, is counter-current. In the reactor 400' shown in FIG. 5B, the relationship between the directions 460 and 470' of fluid flow in the channels and second gaps, respectively, is co-current.

As shown in FIGS. 1B, 3C, and 4B, the total area of the seven tubes in FIG. 1B is 67 square inches, and the total channel cross-sectional section area in FIG. 3C and FIG. 4B are also 67 square inches. However, the diameter of the shell-and-tube reactor containing seven reactor tubes is 20 inches, giving rise to a large dimension compared to the two channel reactors. Further, the shell-and-tube reactor also has a large part count compared to the cylindrical shell reactor containing rectangular channels (as depicted in FIGS. 1B and 3C).

In FIG. 3C, the reactor contains multiple channels of different widths in a cylindrical shell. This configuration is preferred for pressurized operations.

In FIG. 4B, multiple macro-channels with the same dimensions are packed inside a square shell. The total cross-sectional area of the channels in FIG. 4C is the same as those in FIGS. 1B and 3C. However, the packing of the channels in the square shell is more compact compared to the packing of the channels in the cylindrical shells. Optionally, the square shell includes additional structural supports to improve its strength for high pressure applications. In some forms, the cross-sectional area of the shell of the reactor can be rectangular. As a non-limiting example, a proposed industrial scale chemical reactor can be a rectangular reactor with a shell dimension at least 30 cm (or 1 ft). The shell contains one or more channels, where each channel has a rectangular cross-sectional area having a first internal dimension, h, greater than 1 cm (0.4 inch) and less than 15 cm (6 inches); preferably between 2.5 cm (or 1 inch) and less than 12.5 cm (5 inches), inclusive, e.g. 10 cm (4 inches); and a second internal dimension, W, between 30 cm (1 ft) and 10 m (32.8 ft), inclusive, preferably between 30 cm (1 ft) and 2 m (6.6 ft), inclusive, or between 30 cm (1 ft) and 1 m (3.3 ft), inclusive. The channel is packed with a catalyst bed(s). In some forms, W is much larger than h, and both h and W are greater than 1 cm, which is the upper dimension limit of most micro-channel reactors.

Design details of two reactors with shells having square cross-sections, and containing one or more channels with rectangular cross-sections are shown in Table 2. The shell volume utilizations by the channels of these reactors are compared with those of the tubes of shell-and-tube reactor (with a shell and tubes with round cross-sections) of the same total channel and tube volumes. In order to achieve the same productivity, the reactors are assumed to have the same reactor length and reactor volume. The reactor length can be measured as the distance between the inlet of the channel (where the reactants enter) and the outlet where the product fluid exits the channel and the reactor.

Referring to Table 2, the reactor denoted Case 2 (i.e., macro-channel reactor filled with packed bed catalyst) has the same reactor volume (0.37 m$^3$) as the shell-and-tube reactor, Case 1, but Case 2 only needs 12 channels instead of the 124 tubes in Case 1. Thus compared to Case 1, Case 2's reactor has a part count reduction factor of 10 (i.e. 124 tubes/12 channels). The reactor denoted Case 3 has a copper MFEC with 16 times higher thermal conductivity compared to the thermal conductivity obtained in the packed bed (Case 2) and a reduced number of channels—three. This reduction in the number of channels in Case 3 gives rise to a part count reduction factor of 41 (i.e. 124 tubes/3 channels).

In larger reactors, the part count reduction can be very large. For example Shell's Pearl FTS unit with Fischer-Tropsch liquid production rate of 140,000 bpd in Qatar has 24 reactors and 29,000 FTS reactor tubes in total. Accordingly, if Shell's Pearl FTS unit was replaced with one or more macro-channel reactors filled with packed bed catalyst (such as described in Case 2) or one or more macro-channel reactors with MFEC (such as described in Case 3), the part count reduction and resulting manufacturing cost reduction would be very significant: a single channel could replace dozens to hundreds of tubes.

In Cases 2 and 3, multiple macro-channels with the same dimensions are packed inside a square shell. The total cross-sectional areas of the channels of Cases 2 and 3 are the same as that in Case 1. But the square shell is more compact compared to reactors with cylindrical shells. Schematics of reactors with cylindrical shells are shown in FIGS. 1B, 3A, and 3C.

However, square shells or channels, compared with cylindrical shell or tubes, can have lower mechanical strength. Optionally, the square shell and channels include additional structural supports outside the shells and/or channels to improve their strength for high pressure applications. Alternatively, lower pressure differentials (i.e., pressure difference between the inside of a channel, shell, or both, and a space surrounding the channel, shell, or both) are preferable to reduce the mechanical strength and wall thickness requirements, especially for the channels. For example, even when a reaction is operated at 20 atm inside the channels ($P_i$), the channel wall thickness can still be very thin as long as the pressure differential between the shell side ($P_o$) and the channel side is low enough. Exemplary low pressure differentials can be less than 20 atm, preferably less than 10 atm or 5 atm.

TABLE 2[a]

Comparison between the tube-shell reactor, macro-channel reactor and macro-channel reactor filled with MFEC.

| | Case 1 Shell-Tube Reactor (Base Case) | Case 2 Macro-Channel | Case 3 Macro-Channel + MFEC |
|---|---|---|---|
| Shell Shape | Round | Square | Square |
| Shell dimension (m) | 0.5 (diameter) 6.00 (length) | 0.30 (height) 0.30 (width) 6.00 (length) | 0.30 (height) 0.30 (width) 6.00 (length) |
| Tube/channel gap (mm) | 7 | 7 | 28 |
| Shell volume $V_s$ (m$^3$) | 1.18 | 0.55 | 0.55 |
| Volume reduction factor | 1.0 | 2.2 | 2.2 |
| Tube/channel shape | round | rectangle | rectangle |
| Tube or channel cross-section dimensions | 25 mm (diameter) | 17.7 mm (height) 0.290 m (width) | 71 mm (height) 0.290 m (width) |
| Tube/channel count | 124 | 12 | 3 |
| Part count reduction | 1 | 10 | 41 |
| Tube or channel volume $V_r$ (m$^3$) | 0.37 | 0.37 | 0.37 |
| Shell Volume Utilization ($V_r/V_s$) | 0.31 | 0.68 | 0.68 |

[a]Assume the gap size of 7 mm is determined by the energy balance for heat transfer in Case 2 (i.e., macro-channel with packed bed catalyst). The gap size also meets the requirement for easy machining in Case 1. It is also assumed that the shell width is the channel width plus 14 mm (2 × 7 mm) and the shell height is the product of channel count times the total of the channel height and the gap height. In Case 3, the gap size becomes four times larger in order to have the same heat exchange fluid flow rate and the same heat transfer capacity.

Calculations show that the estimated shell volume utilization can be as high as 68%, as shown in Table 2. If these channels are filled with catalyst particles at a common solid fraction of 60%, the catalyst loading fraction will be 41% of the shell volume, which is almost 10 times higher than the catalyst loading of typical wash-coated channel reactors. The shell volume utilization of the macro-channel reactor is twice that of the shell-and-tube reactor, as shown in Table 2. For a given reactor volume, higher shell volume utilization means a smaller shell size, as shown in Table 2. The macro-channel reactor approach provides a two-fold reduction in shell volume and nearly 10-fold (Case 2) reduction in part count. Therefore, this design provides an opportunity to improve the process intensification of the FTS process.

Referring to Table 2, by way of a further example, an exemplary shell-and-tube reactor may contain 124 tubes each having a diameter of 25 mm (about 1 inch), while a macro-channel reactor will need just 12 channels with a cross-section dimension of 17.7 mm×0.29 m to convert the same reactants to the same product at the same rate. The MFEC based macro-channel reactor (e.g., copper MFEC) can further reduce the part count to three with a corresponding 41-fold part count reduction compared to the shell-and-tube reactor.

Both of the reactor shells containing the macro-channel reactors are more compact than the pilot FTS reactor. They are smaller (i.e., have a smaller shell volume) than the 0.50-m diameter round shell used in the exemplary pilot FTS reactor described in Table 1.

As shown in Table 2, the macro-channel reactor filled with MFEC has a shell volume utilization of 67% (i.e., ⅔), which is twice the value obtained with typical shell-and-tube reactors.

9. Catalyst Loading Capacity

The macro-channel approach significantly improves the utilization of microfibrous media, which allows for increased catalyst loading capacity compared to wash-coating the catalyst on the walls of the channel or tube. Macro-channel reactors can boost the microfibrous media utilization to at least 90%, at least 95%, at least 98%, optionally to almost 100%.

Optionally, the catalyst occupies between 1% and 60% of the volume of the channel. For reactors used in Fischer-Tropsch Synthesis, the catalyst is a Fischer-Tropsch catalyst.

The macro-channel reactors described herein can further reduce the part count by including channels with larger dimensions. For example, the FTS reactor tube diameter can be as large as 4 inches when the catalyst activity is similar or even slightly higher than the one used inside the shell-and-tube reactor, where tube diameter is limited to 1 inch. When a microfibrous entrapped catalyst (MFEC) is packed inside the macro-channels, the channel height can be as high as 2.8 inches (about 71 mm), achieving a shell volume utilization of 68% at a channel gap of 28 mm, i.e., almost 68% of the shell volume is used in the FTS reaction.

10. Heat Exchange Efficiency

The dimensions of the channels give rise to improved heat exchange between a fluid in the channel and a fluid in a gap. The widths are generally greater than the heights to provide a large surface area for heat exchange over the surface(s) of the width(s).

In some forms, the channels contain a microfibrous entrapped catalyst that can also transfer thermal energy within the channels to the walls. When such a catalyst is present, the height of the channel can be much larger than a channel with a packed bed catalyst due to the higher thermal conductivity of the bed in the channel. For reactors containing a microfibrous entrapped catalyst bed in the channel, the thermal conductivity of the bed can be increased by about 50 to 200 times compared to the thermal conductivity of a packed bed catalyst in the same channel, for example the thermal conductivity of the bed can be at least 50 times, at least 60 times, at least 70 times, at least 80 times, at least 90 times, at least 100 times greater that the thermal conductivity of a packed bed catalyst in the same channel. The heat transfer coefficient can also be increased by about three to five times, compared to a packed bed catalyst in the same channel.

III. Methods for Using the Reactors

The industrial scale chemical reactors described herein can be used in a variety of endothermic or exothermic reactions. A particular example of an exothermic reaction is the FTS reaction. Accordingly, the reactor can be included in a plant for making longer chain hydrocarbons from natural gas. Optionally, the plant can include a means for forming synthesis gas, and means for performing the FTS reaction. This process can be carried out at an oil-producing facility connected to one or more oil wells, for example to treat a fluid stream associated with the one or more wells. Several other exemplary applications include methanol synthesis from syngas, hydrogenation reactions, hydrocarbon partial oxidation, etc.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other embodiments the values may range in value either above or below the stated value in a range of approx. +/−5%; in other embodiments the values may range in value either above or below the stated value in a range of approx. +/−2%; in other embodiments the values may range in value either above or below the stated value in a range of approx. +/−1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

We claim:

1. An industrial scale chemical reactor comprising:
   a shell defined by one or more walls, wherein each wall comprises an inner surface;
   two or more rectangular channels inside the shell, wherein each internal dimension of the channel is greater than 10 mm;
   a catalyst bed inside the channel, wherein catalyst particles or pieces containing catalyst particles are packed in the bed;
   a first gap between the channel and the inner surface of the wall; and
   a second gap between adjacent channels.

2. The reactor of claim 1, wherein the shell has a circular or square cross-section.

3. The reactor of claim 1, wherein the total volume of the channel is more than 50% of the shell volume.

4. The reactor of claim 1, comprising two or more rectangular channels, and wherein the channels are aligned in the same direction.

5. The reactor of claim 1, wherein the channel is formed from a metal, metal alloy, or ceramic with a thermal conductivity between 10 W/m·K and 4000 W/m·K, inclusive.

6. The reactor of claim 1, wherein the channel has a first internal dimension and a second internal dimension, wherein the first internal dimension is the height of the channel, wherein the second internal dimension is the width of the channel, and wherein the second internal dimension is larger than the first internal dimension.

7. The reactor of claim 6, wherein the height of the channel is greater than 10 mm and less than 150 mm.

8. The reactor of claim 7, wherein the width of the channel is greater than 250 mm.

9. The reactor of claim 6, wherein the second internal dimension is between three and 400 times, inclusive, larger than the first internal dimension.

10. The reactor of claim 6, wherein the height of the channel is in the range of 60% to 80% of the diameter of a tube in a tubular reactor that has the same production rate, the same reactor length, the same volume as the channel, and is filled with the same catalyst.

11. The reactor of claim 1, wherein the second gap is smaller than the first gap.

12. The reactor of claim 1, wherein the second gap is at least 5 mm or at least 10 mm.

13. The reactor of claim 1, further comprising a heat exchange fluid flowing through the first gap and the second gap.

14. The reactor of claim 13, further comprising a fluid flowing through each of the two or more channels, wherein the heat exchange fluid and the fluid in the channel flow in a co-current pattern, a counter-current pattern, or a cross-current pattern, or a combination thereof.

15. The reactor of claim 1, further comprising a support structure between adjacent channels or between the channels and the walls of the shell, or both, wherein the support structure is located in the first gap or in the second gap.

16. The reactor of claim 15, wherein each support structure is independently selected from the group consisting of metal bars, plates, brackets, and rods.

17. The reactor of claim 1, wherein the bed is a packed bed and comprises catalyst in the form of extrudates, pellets, rings, powder, or grains, or a combination thereof.

18. The reactor of claim 1, wherein the bed comprises microfibrous entrapped catalysts, catalyst rings, metal foam, or ceramic foam, or a combination thereof.

19. The reactor of claim 1, wherein the shell is made from a material selected from the group consisting of metal, metal alloys, ceramics, and glass.

20. The reactor of claim 1, wherein the catalyst bed is packed with a secondary heat transfer structure with an effective thermal conductivity greater than 10, 20, or 50 W/m·K.

21. The reactor of claim 1, wherein the bed comprises microfibrous entrapped catalysts.

* * * * *